United States Patent [19]

Teagarden et al.

[11] Patent Number: 5,741,523
[45] Date of Patent: Apr. 21, 1998

[54] STABILIZED PROSTAGLANDIN E1

[75] Inventors: Dirk L. Teagarden; William J. Petre, both of Kalamazoo; Paul M. Gold, Vicksburg, all of Mich.

[73] Assignee: Pharmacia & Upjohn Company, Kalamazoo, Mich.

[21] Appl. No.: 619,690

[22] PCT Filed: Sep. 6, 1994

[86] PCT No.: PCT/US94/09648

§ 371 Date: Mar. 28, 1996

§ 102(e) Date: Mar. 28, 1996

[87] PCT Pub. No.: WO95/11683

PCT Pub. Date: May 4, 1995

Related U.S. Application Data

[63] Continuation-in-part of Ser. No. 143,695, Oct. 27, 1993, abandoned.

[51] Int. Cl.⁶ .................... A61K 31/557; A61K 9/14
[52] U.S. Cl. ............... 424/489; 424/400; 514/559; 514/573
[58] Field of Search .................. 514/559, 560, 514/573; 424/400, 489

[56] References Cited

U.S. PATENT DOCUMENTS 3,927,197  12/1975  Moonkhouse ............... 424/45
3,952,004  4/1976  Moonkhouse ............... 260/308 D
4,113,882  9/1978  Okazaki ..................... 424/317
5,082,664  1/1992  Lenk ......................... 424/450

OTHER PUBLICATIONS

Congres International de Technologie Pharmaceutique, P.P. Deluca et al., "Acceleration of Freeze–Drying Cycles of Aqueous Solutions of Lactose and Sucrose With Tertiary Butyl Alcohol", 574, vol. 1, pp. 439–447 (1989).

*Primary Examiner*—Gollamudi S. Kishore
*Attorney, Agent, or Firm*—Donald L. Corneglio

[57] ABSTRACT

A stable and lyophilized formulation of prostaglandin E-1 made by the process comprising a) dissolving PGE-1 in a solution of lactose and tertiary butyl alcohol wherein said tertiary butyl alcohol is present in an amount of from about 15% to about 33% volume/volume and the ratio of said lactose to PGE-1 is from about 40.000 to 1 to about 10.000 to 1 weight/weight whereby a formulation of PGE-1dispersed in lactose is formed; b) adjusting and maintaining the pH of said formulation from about 3.5 to about 6 with an organic acid buffer; c) freezing said formulation to about −50° C.; and d) drying said formulation to obtain a moisture content of less than 1% by dry weight and a tertiary butyl alcohol content of less than 3% by dry weight. Preferably, step c) includes after freezing said formulation to about −50° C., warming to about −25° C. for about 2 hours then refreezing to about 50° C. Preferably, the prostaglandin is in an amount of about 25 to 100 ppm in lactose and the pH is maintained at about 4 to 5.

3 Claims, No Drawings

STABILIZED PROSTAGLANDIN E1

This continuing application is the national phase of international application PCT/US94/09648, filed Sep. 6, 1994, which was a continuation-in-part of U.S. Ser. No. 08/143,695 filed 27 Oct., 1993, now abandoned.

BACKGROUND OF THE INVENTION

Prostaglandin $E_1$ (PGE-1) is an inherently unstable compound. PGE-1 is chemically (11α, 13E, 15S )-11,15-dihydroxy-9-oxoprost-13-en-1-oic acid; or 3-hydroxy-2-(3-hydroxy-11-octenyl)-5-oxo-cyclopentaneheptanoic acid; and is commonly referred to as alprostadil or $PGE_1$. PGE-1 is a primary prostaglandin which is easily crystallized from purified biological extracts. A goal of this invention was the development of a room temperature stable formulation of PGE-1. More preferred would be a method to stabilize a low dose (5–20 μg) formulation of PGE-1 suitable for use in the treatment of erectile dysfunction.

Various attempts to freeze-dry PGE-1 have been described in U.S. Pat. Nos. 3,952,004 and 3,927,197. The first patent '004 describes the stabilization of PGE-1 in tertiary butyl alcohol and sodium chloride and that lactose or other "simple sugars" destabilize PGE-1. The second patent '197 describes PGE-1 stabilized with tertiary butyl alcohol.

Despite various attempts to stabilize PGE-1, better and more effective methods are in demand to increase shelf life and maintain efficacy. PGE-1 formulations in lactose appears to degrade through an apparent second order mechanism with respect to $PGE_1$ concentration in the solid state. Maximum stability can be achieved by either minimizing the PGE-1 concentration in a suitable lactose diluent or by optimizing other parameters which may impact the second order rate constant. The second order rate constant is affected by the solid state pH, the buffer content, the moisture content, the use of tertiary butyl alcohol during processing, the freezing rate, and the drying rate. All of these parameters have been optimized to minimize the value of the second order rate constant.

SUMMARY OF THE INVENTION

In one aspect the subject invention is a lyophilized formulation of PGE-1 made by the process comprising:

a) dissolving PGE-1 in a solution of lactose and tertiary butyl alcohol wherein the tertiary butyl alcohol is present in an amount of from about 15% to 33% volume/volume and the ratio of lactose to PGE-1 is from about 40,000 to 1 to about 10,000 to 1 weight/weight (25 to 100 ppm in lactose) whereby a formulation of PGE-1dispersed in lactose is formed;

b) adjusting and maintaining the pH of the formulation from about 3.5 to about 6 with an organic acid buffer (preferably sodium citrate);

c) freezing the formulation to about −50° C.; and d) drying the formulation to obtain a moisture content of less than 1% by dry weight and a tertiary butyl alcohol content of less than 3% by dry weight.

Preferably, the PGE-1 in the formulation is in an amount of about 25 to 100 ppm lactose and the pH is adjusted and maintained at 4 to 5 by the presence of a buffer. Preferably, the freezing step (c) includes an annealing process by freezing the formulation to about −50° C., warming to about −25° C. for about 2 hours then refreezing to about −50° C.

In another aspect, the subject invention is a method for preparing a stabilized, lyophilized formulation of PGE-1 comprising the steps set forth above.

In yet another aspect, the present invention is a freeze-dried formulation of PGE-1 for use in the treatment of erectile dysfunction. Typical dosages of the formulation are (5–20 μg) formulations of PGE-1. These formulations correspond to a ratio of lactose to PGE-1 of from about 40,000 to 1 to about 10,000 to 1 weight/weight (25 to 100 ppm in lactose). That is, 5 μg corresponds to 40,000 to 1; 10 μg corresponds to 20,000 to 1 and 20 μg corresponds to 10,000 to 1.

DETAILED DESCRIPTION OF THE INVENTION

The subject invention is a lyophilized PGE-1 composition made from a bulk sterile filtered solution which contains 20% v/v tertiary butyl alcohol (TBA) and has an apparent pH of approximately 4. Both the water and TBA are removed during the freeze-drying process. Residual water and TBA remaining after lyophilization are <0.5% and 0.5–2% respectively of the dried cake mass. In one formulation, a vial dosage contains after completion of lyophilization: 23 μg of PGE-1 (alprostadil), 193.8 mg of anhydrous lactose, and 53 μg of sodium citrate. After reconstitution of this freeze-dried powder with 1.0 ml of either water for injection or bacteriostatic water for injection, a solution containing 20 μg/ml of PGE-1 is obtained. The freeze-dried powder is packaged in a 5 ml vial and sealed with a lyophilization style closure within the freeze-dry chamber, and capped with an aluminum overseal. The chemical stability of the PGE-1 can be predicted by use of the Arrhenius equation and accelerated stability data. Initial rate kinetic analyses (i.e., monitoring the rate of formation of the major degradation product, $PGA_1$) can be used to assess the chemical stability. The projected stability analysis indicates that when the product is properly manufactured with the optimized formulation and process, the shelf-life should be greater than 24 months when the product is stored at 25° C. or less.

Initial work centered on the use of a lactose diluent and lyophilization from a tertiary butyl alcohol (TBA)/water co-solvent system. The freeze-dried formulation produced appeared to possess the properties of a solid solution. The degradation of the PGE-1 in this type of formulation could be best described by a second order mechanism. Stability could be increased by maximizing the amount of lactose diluent or minimizing the amount of PGE-1 present. The solid state second order kinetics fit well to an Arrhenius type temperature relationship. Residual moisture was shown to have a deleterious effect on the stability. The pH of the cake also affected the stability. Optimum stability was achieved at about pH 4–5. A minimum amount of citrate buffer was added to the formula to control pH. Lyophilization from a TBA/water co-solvent mixture improved stability of the formulations compared to water only. Typically, standard freeze drying techniques can be used to prepare the stabilized PGE-1. More preferably, an annealing technique can be performed to decrease and more uniformly control the residual tertiary butyl alcohol in the freeze dried product. Optimum stability was achieved when freeze-drying from a 17–25% TBA/water mixture.

The method for preparing a stabilized, freeze-dried formulation of PGE-1 controls key parameters which affect product stability including the following: the level of lactose diluent present, the apparent pH of the lyophilized cake, the moisture content, the use of the co-solvent tertiary butyl alcohol during processing, the freezing rate and methodology prior to lyophilization, the freeze-drying rate, and the size of the vial used to manufacture the product.

Lyophilization of a buffered lactose formulation of PGE-1 from a tertiary butyl alcohol (TBA)/water mixture provides superior product stability than when freeze-drying from only an aqueous system. The level of TBA which afforded the product maximum stability appeared to be when the TBA amount ranged from 17–25% (v/v). The 20% TBA level was selected as the amount of co-solvent for the PGE-1 formulation since it fell within the optimum co-solvent range. The lower the level of TBA used also reduced the flammability potential, reduced the amount of TBA waste which would be generated after lyophilization, reduced the level of isopropyl alcohol (a process impurity in the TBA) in the product, and lowered the precipitation potential during manufacturing for the lactose from the co-solvent system. Stability data clearly indicated that lyophilization of the buffered lactose formulation of PGE-1 from a TBA/water co-solvent system would be significantly more stable than freeze-drying from an aqueous system. The mechanism for the improvement in stability when using the TBA is unknown but it is likely enabling the PGE-1 molecules to be kept further apart during the freezing and lyophilization phases of manufacture. Therefore, it is recommended that the final formulation be lyophilized from a co-solvent system containing 20% v/v TBA. It is important that this level of TBA be used because lower levels of TBA (≦17%) in the final formulation will produce a product which is much less stable than when using at least 20% TBA.

The resulting residual TBA in the final product is expected to be approximately 0.5 to 2% of the cake weight. A safety assessment of TBA and its impurities (isopropyl alcohol, 2-butyl alcohol, and isobutyl alcohol) concluded that TBA levels of not more than 3% of a 200 mg freeze-dried cake was acceptable and that other residual organic solvents should be not more than 0.5% of a 200 mg freeze-dried cake.

The application of heat to the lactose may adversely affect product stability. The stability data clearly dictates that close control of the freeze-dry cycle (both primary and secondary drying) is critical to reproducible manufacture lots with equivalent stability. Stability can therefore be a function of processing parameters.

Since the PGE-1 degradation kinetics fit (at least empirically) a second order mechanism, stability can be improved by simple dilution of the PGE-1 with lactose. This would suggest that maximizing the amount of lactose for a given amount of PGE-1 should provide the optimum stability. For a 20 µg/ml formulation of PGE-1 the amount of lactose chosen for formulating the optimum formulation is 204 mg of lactose monohydrate. After lyophilization, the 5% water is removed and the resulting lactose present in the vial is 193.8 mg. The cake volume for 193.8 mg of anhydrous lactose is approximately 0.13 ml. Therefore, the theoretical solution concentration of lactose after reconstitution with 1.0 ml is (193.8 mg/1.13 ml) or 172 mg/ml. The amount of PGE-1 needed to produce a 20 µg/ml solution after reconstitution with 1.0 ml is (1.13 ml×20 µg/ml) or 22.6 µg.

It has been determined that the cake pH also affected product stability. Maximum stability is achieved when the cake pH is held near pH 4 to 5. Both citrate and acetate buffers can be used; however, citrate buffer was selected as the buffer of choice for the PGE-1 formula since it is a common buffer for parenteral products. Since PGE-1 is susceptible to both acid and base hydrolysis, it is probable that some buffer catalysis of the PGE-1 molecule may occur. The amount of citrate buffer selected for the final formulation was chosen based on a compromise between sufficient buffer to adequately control pH and yet not itself significantly provide an alternate catalytic route. The level of citrate chosen for the final formulation was 53 µg of sodium citrate/23 µg PGE-1 (3.17 moles citrate/mole PGE-1). This level of citrate will theoretically cause only a relatively minor increase (<7%) in the degradation rate constant. In order to determine if sufficient buffer was present to control pH for the shelf life of the product, samples with this amount of buffer present were degraded to less than 90% of initial potency under accelerated conditions. The pH was measured initially and after the >10% drop in potency had taken place. No significant change in pH occurred. This demonstrates that sufficient buffer was present to maintain pH during the normal shelf life of the product where less than 10% degradation will take place.

The presence of moisture in the product will have a negative impact on product stability. It is therefore preferred that the formulation have the level of moisture as low as possible during the processing and to maintain that level throughout the shelf life of the product.

The rate of freezing also has an effect on product stability. The unique kinetics of the degradation pathway indicates that it is imperative that the PGE-1 molecules be kept as far apart as possible in order to minimize the interaction of two PGE-1 molecules. Typically, the lyophilization cycle is designed to proceed as fast as possible without exceeding the melting temperature of the frozen solution during primary drying. Therefore, as long as no meltback occurs during the primary drying phase and the water content is reduced to a sufficiently low level during the secondary drying phase, then the product would normally be acceptable. However, the PGE-1 formulation can be quite different from the normal situation because the major component in the formulation is lactose. The literature reports that lactose possesses a very low glass transition temperature ($T_g$) which is on the order of −31° C. It is possible to lyophilize above the glass transition temperature for an excipient such as lactose without exceeding the melting temperature of the bulk solution. If the product temperature exceeds $T_g$, the frozen solution viscosity decreases significantly resulting in a rubbery system where the mobility of the PGE-1 molecules will increase substantially. This type of event could lead to a situation where the PGE-1 molecules could either aggregate, micellize, or come into closer proximity than if the frozen solution is kept below the $T_g$. It is important, therefore, that the drying cycle be optimized to prevent such an occurrence from happening.

Typically, the PGE-1 in lactose formulation is freeze dried using standard techniques. More preferred, an annealing process is used to enable the residual tertiary butyl alcohol to be reduced and controlled. In an annealing process the initial stage of the freeze drying process is carried out by freezing the PGE-1 formulation to about −50° C., warming it to about −25° C. for about 2 hours then refreezing it to about −50° C. Next, the freeze drying is continued to obtain a moisture content of less than 1% by dry weight and a tertiary butyl alcohol content of less than 3% by dry weight.

The conclusion is that in order to achieve the proper product stability, not only must the formulation be carefully chosen, but also the manufacturing process must be appropriately optimized. The mechanisms may not be fully understood on a theoretical basis at this time, however, the effects described are reproducible. It is therefore, mandated that a conservative cycle be used to consistently achieve maximum product stability.

Prototype lactose base formulations of PGE-1 indicated that the stability correlated well with an Arrhenius type temperature relationship. This fit to an Arrhenius relationship was apparent whether the rate constants were plotted for the degradation rate of PGE-1 or for the rate of formation of the major degradation product $PGA_1$. Therefore, the stability of the lactose formulation for PGE-1 can be accurately assessed by initial rate type kinetic analysis (i.e., by monitoring the rate of $PGA_1$ formation).

Optimization of a freeze-dried formulation PGE-1 (Alprostadil S.Po.) and preferably as designed for use in an injectable such as in the treatment of erectile dysfunction has been determined as explained above. The formulation appears to degrade through an apparent second order mechanism with respect to PGE-1 concentration in the solid state. Maximum stability can be achieved by either minimizing the PGE-1 concentration in the lactose diluent or by optimizing those parameters which impact the second order rate constant. The amount of lactose diluent chosen for the optimized formulation was based on solubility limitations and the irritation potential of the lactose. In one embodiment the amount of PGE-1 present was based on the proposed clinical dose for an injection volume of 1 ml or less. The second order rate constant is affected by the solid state pH, the buffer content, the moisture content, the use of tertiary butyl alcohol during processing, the freezing rate, and the drying rate. All of these have been optimized to minimize the value of the second order rate constant. The product is lyophilized from a bulk sterile filtered solution which contains 20% v/v tertiary butyl alcohol (TBA) and has an apparent pH of approximately 4. Both the water and TBA are removed during the freeze-drying process. Residual water and TBA remaining after lyophilization are <0.5% and 0.5 to 2% respectively of the dried cake mass. The final formulation, for example, per vial contains after completion of lyophilization: 23 µg of PGE-1 (alprostadil), 193.8 mg of anhydrous lactose, and 53 µg of sodium citrate. After reconstitution of this freeze-dried powder with 1.0 ml of either water for injection or bacteriostatic water for injection, a solution containing 20 µg/ml of PGE-1 will be obtained. Or, the final formulation, for example, per vial contains after completion of lyophilization: 11.9 µg of PGE-1 (alprostadil), 193.8 mg of anhydrous lactose, and 53 µg of sodium citrate. After reconstitution of this freeze-dried powder with 1.0 ml of either water for injection or bacteriostatic water for injection, a solution containing 10 µg/ml of PGE-1 will be obtained. Or, the final formulation, for example, per vial contains after completion of lyophilization: 6.1 µg of PGE-1 (alprostadil), 193.8 mg of anhydrous lactose, and 53 µg of sodium citrate. After reconstitution of this freeze-dried powder with 1.0 ml of either water for injection or bacteriostatic water for injection, a solution containing 5 µg/ml of PGE-1 will be obtained. The freeze-dried powder, as per these examples, is packaged in a 5 ml vial, sealed with a lyophilization style closure within the freeze-dry chamber, and capped with an aluminum overseal. The chemical stability of the PGE-1 can be predicted by use of the Arrhenius equation and accelerated stability data. Initial rate kinetic analyses (i.e., monitoring the rate of formation of the major degradation product, $PGA_1$) can also be used to assess the chemical stability. The projected stability analysis indicates that when the product is properly manufactured with the optimized formulation and process, the shelf-life should be greater than 24 months when the product is stored at 25° C. or less.

A lot for the various strengths of PGE-1 stabilized product freeze dried under the conditions described above was prepared and stability measured. The results are shown in the Tables that follow:

TABLE I

20 µg Strength

| Time (months) | Potency at 5° C. (% of Initial) | Potency at 25° C. (% of Initial) |
|---|---|---|
| 0 | 100.5% | 100.5% |
| 0 | 100.0% | 100.0% |
| 0 | 100.5% | 100.5% |
| 0 | 99.5% | 99.5% |
| 0 | 100.0% | 100.0% |
| 3 | 99.5% | 100.5% |
| 3 | 100.5% | 101.5% |
| 6 | 100.0% | 98.5% |
| 6 | — | 100.5% |
| 9 | 99.5% | 96.6% |
| 9 | 99.0% | 98.5% |
| 11.44 | 100.0% | 96.6% |
| 11.44 | 99.5% | 96.6% |
| 11.44 | 99.5% | 96.1% |
| 12 | 99.5% | 97.6% |
| 12 | 100.5% | 97.6% |
| 12 | 101.0% | 97.6% |
| 12 | 101.0% | 97.6% |
| 15 | 101.0% | 96.1% |
| 15 | 102.0% | 95.6% |
| 18 | 100.0% | 95.6% |
| 18 | 99.5% | 94.6% |
| 21 | 99.0% | 96.1% |
| 21 | 99.5% | 95.1% |

TABLE II

10 µg Strength

| Time (months) | Potency at 5° C. (% of Initial) | Potency at 25° C. (% of Initial) |
|---|---|---|
| 0 | 99.1% | 99.1% |
| 0 | 100.9% | 100.9% |
| 0 | 100.0% | 100.0% |
| 0 | 100.0% | 100.0% |
| 0 | 99.1% | 99.1% |
| 0 | 101.9% | 101.9% |
| 0 | 100.9% | 100.9% |
| 0 | 100.9% | 100.9% |
| 0 | 100.0% | 100.0% |
| 0 | 100.0% | 100.0% |
| 1 | 99.1% | 102.8% |
| 1 | 100.0% | 102.8% |
| 1 | 100.0% | 102.8% |
| 2 | 100.9% | 102.8% |
| 2 | 102.8% | 102.8% |
| 2 | 102.8% | 102.8% |
| 3 | 99.1% | 100.0% |
| 3 | 100.9% | 99.1% |
| 3 | 99.1% | 98.1% |
| 4 | 100.9% | 100.9% |
| 4 | 100.9% | 100.9% |
| 4 | 100.9% | 100.0% |
| 5 | 100.0% | 97.2% |
| 5 | 100.0% | 99.1% |
| 5 | 100.0% | 99.1% |
| 6 | 98.1% | 97.2% |
| 6 | 97.2% | 98.1% |
| 6 | 96.3% | 98.1% |
| 7.95 | 97.2% | — |
| 7.95 | 98.1% | — |
| 7.99 | 98.1% | — |
| 7.99 | 98.1% | — |
| 8 | 98.1% | — |
| 8 | 97.2% | — |
| 9 | 101.9% | 99.1% |
| 9 | 100.9% | 99.1% |
| 9 | 102.8% | 100.0% |
| 12 | 98.1% | 97.2% |
| 12 | 98.1% | 96.3% |

TABLE II-continued

10 μg Strength

| Time (months) | Potency at 5° C. (% of Initial) | Potency at 25° C. (% of Initial) |
|---|---|---|
| 12 | 99.1% | 96.3% |
| 15 | 99.1% | 96.3% |
| 15 | 99.1% | 94.3% |
| 15 | 99.1% | 95.3% |

TABLE III

5 μg Strength

| Time (months) | Potency at 5° C. (% of Initial) | Potency at 25° C. (% of Initial) |
|---|---|---|
| 0 | 101.5% | 101.5% |
| 0 | 99.3% | 99.3% |
| 0 | 100.4% | 100.4% |
| 0 | 98.9% | 98.9% |
| 0 | 99.6% | 99.6% |
| 0 | 99.8% | 99.8% |
| 0 | 99.6% | 99.6% |
| 0 | 100.9% | 100.9% |
| 0 | 100.2% | 100.2% |
| 0 | 100.4% | 100.4% |
| 1 | 101.1% | 100.7% |
| 1 | 100.7% | 99.4% |
| 1 | 100.2% | 99.8% |
| 2 | 100.0% | 99.3% |
| 2 | 100.6% | 100.7% |
| 2 | 100.6% | 99.4% |
| 3 | 100.4% | 99.8% |
| 3 | 100.4% | 100.2% |
| 3 | 100.6% | 99.8% |
| 4 | 103.5% | 100.0% |
| 4 | 99.6% | 99.4% |
| 4 | 100.6% | 100.6% |
| 5 | 98.9% | 99.4% |
| 5 | 100.0% | 99.4% |
| 5 | 100.9% | 100.2% |
| 6 | 100.7% | 99.4% |
| 6 | 100.9% | 99.6% |

TABLE III-continued

5 μg Strength

| Time (months) | Potency at 5° C. (% of Initial) | Potency at 25° C. (% of Initial) |
|---|---|---|
| 6 | 100.9% | 100.2% |
| 6 | 100.0% | 99.1% |
| 6 | 99.3% | 98.5% |

The Tables show that excellent stability was maintained for the life of lyophilized product.

What is claimed:

1. A lyophilized formulation of PGE-1 made by the process consisting of:

a) adding PGE-1 to lactose and tertiary butyl alcohol wherein said tertiary butyl alcohol is present in an amount of from about 15% to about 33% volume/volume and the ratio of said lactose to PGE-1 is from about 40,000 to 1 to about 10,000 to 1 weight/weight whereby a formulation of PGE-1 dispersed in lactose is formed;

b) adjusting the pH of said formulation from about 4 to about 5 with a citrate or acetate buffer;

c) freezing said formulation to about −50° C., warming to about −25° C. for about 2 hours then refreezing to about −50° C.; and d) drying said formulation to obtain a moisture content of less than 1% by dry weight and a tertiary butyl alcohol content of less than 3% by dry weight.

2. The lyophilized formulation of PGE-1 made by the process of claim 1 wherein in said organic acid buffer of step b) is sodium citrate.

3. The lyophilized formulation of PGE-1 made by the process of claim 1 wherein in PGE-1 is in an amount of about 25 to about 100 ppm in lactose.

* * * * *